United States Patent [19]

Hughes

[11] Patent Number: 4,535,092
[45] Date of Patent: Aug. 13, 1985

[54] ACYLANILIDES HAVING ANTIANDROGENIC ACTIVITY

[75] Inventor: Leslie R. Hughes, Macclesfield, United Kingdom

[73] Assignee: Imperial Chemical Industries PLC, London, England

[21] Appl. No.: 438,351

[22] Filed: Nov. 1, 1982

[30] Foreign Application Priority Data

Nov. 6, 1981 [GB] United Kingdom ............... 8133613

[51] Int. Cl.³ .................... A61K 31/38; C07D 333/32
[52] U.S. Cl. ..................................... 514/438; 549/61;
549/65; 514/445; 549/76; 549/77; 544/298;
549/436; 549/478; 544/333; 549/479; 549/488;
544/334; 544/335; 546/141; 546/142; 546/146;
546/155; 546/156; 546/158; 546/168; 546/296;
546/298; 546/314; 548/127; 548/129; 548/142;
548/159; 548/170; 548/182; 548/183; 548/187;
548/188; 548/305; 548/337; 548/343; 548/484;
548/486; 548/540; 549/21; 549/53
[58] Field of Search ................ 549/77, 61, 65, 76; 424/275

[56] References Cited

U.S. PATENT DOCUMENTS

| | | | |
|---|---|---|---|
| 1,878,543 | 9/1932 | Rimele et al. | 564/182 X |
| 2,721,216 | 10/1955 | Speeter | 564/170 |
| 3,255,231 | 6/1966 | Green et al. | 564/170 |
| 3,282,939 | 11/1966 | Spivack et al. | 564/170 |
| 3,419,563 | 12/1968 | Knupfer et al. | 564/182 X |
| 3,632,829 | 1/1972 | Schumacher et al. | 564/170 |
| 3,706,796 | 12/1972 | Blake | 564/182 X |
| 3,933,886 | 1/1976 | Saygin | 549/77 |
| 4,049,713 | 9/1977 | Spivack | 564/170 |
| 4,191,775 | 3/1980 | Glen | 564/170 X |
| 4,291,049 | 9/1981 | Bosone et al. | 549/77 |
| 4,386,080 | 5/1983 | Crossley et al. | |

FOREIGN PATENT DOCUMENTS

| | | | |
|---|---|---|---|
| 0071535 | 2/1983 | European Pat. Off. | 549/77 |
| 1160431 | 1/1964 | Fed. Rep. of Germany | 564/182 |
| 40-4921 | 3/1965 | Japan | 564/170 |
| 0135048 | 4/1974 | Japan | 564/182 |
| 345016 | 4/1960 | Switzerland | 564/182 |
| 828695 | 2/1960 | United Kingdom | 564/166 |

OTHER PUBLICATIONS

Kametani et al., "Index Chemicus", vol. 12(1), 1963, Index No. 37,460.
Hughes, "Chemical Abstracts", vol. 99, 1983, col. 99:139755n.

*Primary Examiner*—Glennon H. Hollrah
*Assistant Examiner*—James H. Turnipseed
*Attorney, Agent, or Firm*—Cushman, Darby & Cushman

[57] ABSTRACT

Acylanilides of the formula

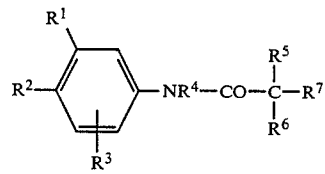

wherein $R^1$, $R^2$ and $R^3$ are substituents defined in claim 1;

wherein $R^4$ is hydrogen or alkyl of up to 4 carbon atoms, or is joined to $R^5$ as stated below;

wherein $R^5$ is hydrogen, hydroxy, or alkoxy or acyloxy each of up to 15 carbon atoms, or is joined to $R^4$ to form an oxycarbonyl group such that together with the —N—CO—C— part of the molecule it forms an oxazolidinedione group;

wherein $R^6$ is alkyl or halogenoalkyl of up to 4 carbon atoms;

and wherein $R^7$ is 5- or 6- membered saturated or unsaturated heterocyclic which contains one, two or three hetero atoms selected from oxygen, nitrogen and sulphur, which heterocyclic may be a single ring or may be fused to a benzo-ring, and which heterocyclic is unsubstituted or bears one or two substituents defined in claim 1;

processes for their manufacture and pharmaceutical compositions containing them. The compounds possess antiandrogenic activity.

9 Claims, No Drawings

ACYLANILIDES HAVING ANTIANDROGENIC ACTIVITY

This invention relates to new amide derivatives and more particularly it relates to novel acylanilides which possess antiandrogenic properties.

According to the invention there is provided an acylanilide of the formula:

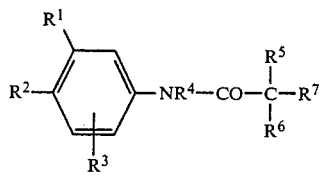

wherein $R^1$ is cyano, carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl;

wherein $R^2$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl;

wherein $R^3$ is hydrogen or halogen;

wherein $R^4$ is hydrogen or alkyl of up to 4 carbon atoms, or is joined to $R^5$ as stated below;

wherein $R^5$ is hydrogen, hydroxy, or alkoxy or acyloxy each of up to 15 carbon atoms, or is joined to $R^4$ to form an oxycarbonyl group such that together with the —N—CO—C— part of the molecule it forms an oxazolidinedione group;

wherein $R^6$ is alkyl or halogenoalkyl of up to 4 carbon atoms;

and wherein $R^7$ is 5- or 6-membered saturated or unsaturated heterocyclic which contains one, two or three hetero atoms selected from oxygen, nitrogen and sulphur, which heterocyclic may be a single ring or may be fused to a benzo-ring, and which heterocyclic is unsubstituted or bears one or two substituents selected from halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; and oxy, which may be an N-oxide or, if the heterocyclic is sufficiently saturated, may be one or two oxo substituents.

It will be observed that the acylanilide derivative of the invention possesses an asymmetric carbon atom, namely the carbon atom which bears the substituents $R^5$, $R^6$ and $R^7$, and it can therefore exist in racemic and optically-active forms. It is to be understood that this invention encompasses the racemic form of the acylanilide derivative and any optically-active forms which possess antiandrogenic activity, it being a matter of common general knowledge how a racemic compound may be resolved into its optically-active forms and how any antiandrogenic activity present in any of these forms may be determined.

A suitable value for $R^1$ or $R^4$ when it is alkyl, or for an alkyl substituent in $R^7$, is, for example, methyl or ethyl.

$R^4$ is preferably hydrogen.

A suitable value for $R^1$ when it is alkoxy or for an alkoxy substituent in $R^7$ is, for example, methoxy or ethoxy.

A suitable value for $R^1$ or $R^2$ when it is alkanoyl, or for an alkanoyl substituent in $R^7$ is, for example, formyl or acetyl.

A suitable value for $R^1$ or $R^2$ when it is alkylthio, alkylsulphinyl, alkylsulphonyl, perfluoroalkyl, perfluoroalkylthio, perfluoroalkylsulphinyl or perfluoroalkylsulphonyl, or for such a substituent in $R^7$ is, for example, methylthio, ethylthio, methylsulphinyl, methylsulphonyl, trifluoromethyl, pentafluoroethyl, trifluoromethylthio, trifluoromethylsulphinyl or trifluoromethylsulphonyl.

A suitable value for $R^3$ when it is halogen, or for a halogen substituent in $R^7$, is fluoro, chloro, bromo or iodo.

$R^3$ is preferably hydrogen or chloro, especially hydrogen.

A suitable value for an alkoxycarbonyl or N-alkylcarbamoyl substituent in $R^7$ is, for example, methoxycarbonyl, ethoxycarbonyl or N-methylcarbamoyl.

A suitable value for $R^5$ when it is alkoxy is, for example, methoxy, ethoxy, propyloxy, n-butyloxy or decyloxy.

A suitable value for $R^5$ when it is acyloxy is, for example, alkanoyl or aroyl each of up to 15 carbon atoms, for example acetoxy, propionyloxy, decanoyloxy, dodecanoyloxy or benzoyloxy.

$R^5$ is preferably hydroxy.

A suitable value for $R^6$ when it is alkyl or halogenoalkyl is, for example, methyl, ethyl, n-propyl, fluoromethyl, difluoromethyl, trifluoromethyl, pentafluoroethyl, chloromethyl, dichloromethyl or trichloromethyl. $R^6$ is preferably methyl.

$R^7$ may be, for example, furyl, thienyl, pyrrolyl, pyridyl, pyrimidinyl, imidazolyl, thiazolyl, thiadiazolyl, benzimidazolyl, benzothiazolyl, indolyl, benzothienyl, benzofuryl, quinolyl, isoquinolyl, 1,2-dihydro-2-oxoquinolyl or 1,3-dithianyl.

A preferred combination of values for $R^1$ and $R^2$ is as follows:

| $R^1$ | $R^2$ |
|---|---|
| trifluoromethyl | nitro |
| trifluoromethyl | cyano |
| chloro | chloro |
| chloro | nitro |
| chloro | cyano |

A preferred acylanilide of the invention has the formula stated above wherein $R^1$ and $R^2$, which may be the same or different, each is cyano, nitro, trifluoromethyl or chloro, $R^3$ and $R^4$ are both hydrogen, $R^5$ is hydroxy, $R^6$ is methyl and $R^7$ is 2-thienyl, 3-thienyl, 2-furyl, 2-thiazolyl, 4-thiazolyl, 5-thiazolyl, 2-benzothiazolyl, 2-pyridyl, 3-pyridyl, 4-pyridyl, 5-pyrimidinyl or 1,3-dithian-2-yl, any of which may be unsubstituted or may bear one halogen (for example fluoro, chloro or bromo), cyano, alkoxy, alkylthio, alkylsulphonyl (for example methoxy, methylthio or methylsulphonyl), trifluoromethyl or oxy substituent.

Specific acylanilides of the invention are hereinafter described in the Examples. Of these, preferred compounds by virtue of their high level of antiandrogenic activity are:

4-nitro-3-trifluoromethyl-, 4-cyano-3-trifluoromethyl- and 3-chloro-4-cyano-N-[2-hydroxy-2-(5-methanesulphonylthien-2-yl)-propionyl]aniline;

4-nitro-3-trifluoromethyl-, 3-chloro-4-cyano- and 4-cyano-3-trifluoromethyl-N-[2-hydroxy-2-(2-chlorothiazol-5-yl)propionyl]-aniline;

4-nitro-3-trifluoromethyl-, 4-cyano-3-trifluoromethyl- and 3,4-dichloro-N-[2-hydroxy-2-(6-cyanopyrid-3-yl)propionyl]aniline;

4-nitro-3-trifluoromethyl-, 4-cyano-3-trifluoromethyl- and 3-chloro-4-cyano-N-[2-hydroxy-2-(6-chloropyrid-3-yl)propionyl]aniline; 4-nitro-3-trifluoromethyl, 3-chloro-4-cyano and 4-cyano-3-trifluoromethyl-N-[2-hydroxy-2-(6-fluoropyrid-3-yl)propionyl]aniline; and 4-nitro-3-trifluoromethyl-, 3,4-dichloro- and 3-chloro-4-cyano-N-[2-hydroxy-2-(pyrimid-5-yl)propionyl]aniline.

The acylanilides of the invention may be manufactured by any chemical process known to be suitable for the manufacture of chemically-analogous compounds.

A preferred process for the manufacture of an acylanilide of the invention wherein $R^5$ is hydroxy comprises the reaction of a compound of the formula:

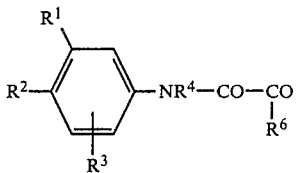

wherein $R^1$, $R^2$, $R^3$, $R^4$ and $R^6$ have the meanings stated above, with an organometallic compound of the formula $R^7$-M, wherein $R^7$ has the meaning stated above and M is a metal radical, for example the lithium radical.

The last-mentioned reaction is preferably carried out in an inert solvent, for example diethyl ether or tetrahydrofuran, at a low temperature, for example at between −70° C. and −100° C.

An alternative process for the manufacture of an acylanilide of the invention comprises the reaction of an amine of the formula:

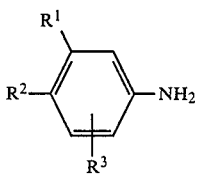

wherein $R^1$, $R^2$ and $R^3$ have the meanings stated above, with an acid of the formula:

$$HO_2C-CR^5R^6-R^7$$

wherein $R^5$, $R^6$ and $R^7$ have the meanings stated above, or with a reactive derivative of said acid.

A suitable reactive derivative of an acid is, for example, an acid anhydride, or an acyl halide, for example an acyl chloride, or a lower alkyl ester of said acid, for example the methyl or ethyl ester.

An acylanilide of the invention wherein $R^4$ and $R^5$ are joined together to form a carbonyl-oxy group, that is, an oxazolidinedione, may be prepared by the reaction of an isocyanate of the formula:

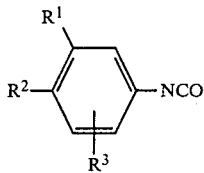

wherein $R^1$, $R^2$ and $R^3$ have the meanings stated above, with an ester of the formula:

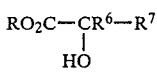

wherein $R^6$ and $R^7$ have the meanings stated above, and wherein R is alkyl of up to 6 carbon atoms, for example methyl or ethyl. This reaction is preferably carried out in an organic solvent, for example diethyl ether, at laboratory temperature.

An acylanilide of the invention wherein $R^5$ is hydroxy may be prepared by the hydrolysis of the corresponding acylanilide wherein $R^5$ is acyloxy, and an acylanilide of the invention wherein $R^5$ is hydroxy and $R^4$ is hydrogen may be prepared by the hydrolysis of the corresponding oxazolidinedione, which may be prepared as described in the preceding paragraph.

An acylanilide of the invention wherein $R^4$ is alkyl may be prepared by the alkylation of the corresponding acylanilide wherein $R^4$ is hydrogen.

An acylanilide of the invention wherein $R^5$ is acyloxy may be prepared by the acylation of the corresponding acylanilide wherein $R^5$ is hydroxy.

An oxazolidinedione of the invention, wherein $R^4$ and $R^5$ are joined together to form a carbonyloxy group, may be prepared by the reaction of the corresponding acylanilide wherein $R^4$ is hydrogen and $R^5$ is hydroxy with phosgene ($COCl_2$).

An acylanilide of the invention wherein one or more of $R^1$, $R^2$ and a substituent in $R^7$ is alkylsulphinyl, perfluoroalkylsulphinyl or phenylsulphinyl, or is alkylsulphonyl, perfluoroalkylsulphonyl or phenylsulphonyl, may be prepared by the oxidation of the corresponding acylanilide wherein one or more of $R^1$, $R^2$ and a substituent in $R^7$ is alkylthio, perfluoroalkylthio or phenylthio, respectively. The oxidising agent and conditions used will determine whether a sulphinyl or a sulphonyl compound is obtained. Thus, oxidation with sodium metaperiodate in methanol solution at or below laboratory temperature will generally convert a thio compound into the corresponding sulphinyl compound; and oxidation with hydrogen peroxide in acetic acid solution or with a persulphate in aqueous solution, at or above laboratory temperature, will generally convert a thio compound into the corresponding sulphonyl compound.

An acylanilide of the invention wherein $R^7$ is nitrogen-containing heterocyclic may be converted into the N-oxide thereof by oxidation with, for example, a peracid, for example, m-chloroperbenzoic acid.

As stated above, an acylanilide of the invention possesses antiandrogenic properties as demonstrated by its ability to decrease the weight of the seminal vesicles of a mature male rat when administered orally for 4 successive days. An acylanilide of the invention may therefore be used in the treatment of, for example, benign prostatic disease or of androgen dependent disease conditions, such as acne, hirsutism or seborrhoea, in warm-blooded vertebrates including man. It may also be used to improve ovulation in a domestic animal.

At a dose of an acylanilide of the invention which produces antiandrogenic activity in rats no symptoms of toxicity are apparent.

The acylanilide of the invention may be administered to a warm-blooded animal in the form of a pharmaceutical or veterinary composition which comprises the acylanilide in association with a pharmaceutically-acceptable diluent or carrier.

The composition may be in a form suitable for oral dosage, as a tablet, capsule, aqueous or oily solution or suspension or emulsion. It may alternatively be in the form of a sterile solution or suspension suitable for parenteral administration, or be in the form of an ointment or lotion for topical administration, or be in the form of a suppository.

The composition may additionally contain one or more drugs selected from anti-oestrogens, for example tamoxifen; aromatase inhibitors, for example testolactone or aminoglutethamide; progestins, for example medroxyprogesterone acetate; inhibitors of gonadotrophin secretion, for example danazol; LH-RH analogues, for example buserelin; cytotoxic agents, for example cyclophosphamide; antibiotics, for example penicillin or oxytetracyclin; and anti-inflammatory agents, for example, especially for topical use, fluocinolone acetonide.

The acylanilide of the invention will normally be administered to a warm-blooded animal at a dose of between 0.1 mg. and 125 mg. per kg. bodyweight.

The invention is illustrated but not limited by the following Examples:

EXAMPLE 1

Pyridine (2.3 ml.) and acetyl chloride (2.1 ml.) were successively added to a stirred solution of 2-hydroxy-2-(thien-2-yl)propionic acid (5 g.) in methylene chloride (50 ml.) and the mixture was stirred at laboratory temperature for 16 hours and then evaporated to dryness. The residue was dissolved in methylene chloride (50 ml.), pyridine (2.3 ml.) and thionyl chloride (2 ml.) were successively added and the mixture was stirred at laboratory temperature for 30 minutes and then evaporated to dryness. The residue was dissolved in pyridine (50 ml.), 3,4-dichloroaniline (4.7 g.) was added and the mixture was stirred at laboratory temperature for 17 hours and then evaporated to dryness. The residue was partitioned between ethyl acetate and dilute aqueous hydrochloric acid and the organic layer was separated, washed successively with dilute aqueous hydrochloric acid, water, saturated aqueous sodium bicarbonate solution and saturated aqueous sodium chloride solution, dried over magnesium sulphate and evaporated to dryness. The residue was dissolved in a 20:1 v/v mixture of ethanol and tetrahydrofuran (50 ml.), aqueous 5% sodium hydroxide solution (12.6 ml.) was added and the mixture was kept at laboratory temperature for 10 minutes and then evaporated to dryness. The residue was partitioned between ethyl acetate and saturated aqueous sodium chloride solution and the organic layer was separated, dried over magnesium sulphate and evaporated to dryness. The residue was purified by chromatography on a silica gel column (150 g.) using a 10:1 v/v mixture of toluene and ethyl acetate as eluant. There was thus obtained N-[2-hydroxy-2-(thien-2-yl)propionyl]-3,4-dichloroaniline, m.p. 122°–123° C.

The 2-hydroxy-2-(thien-2-yl)propionic acid used as starting material was obtained as follows:

A 1.6 molar solution of n-butyl-lithium in hexane (37 ml.) was added to a solution of thiophene (5 g.) in diethyl ether (50 ml.) which was maintained at 0° C., and the mixture was heated under reflux for 6 hours and then cooled to −78° C. A solution of ethyl pyruvate (5.9 g.) in diethyl ether (20 ml.) was added dropwise, the mixture was allowed to warm up to laboratory temperature and saturated aqueous ammonium chloride solution (20 ml.) was added. The mixture was extracted with ethyl acetate and the organic extract was washed with water and then with saturated aqueous sodium chloride solution, dried over magnesium sulphate and evaporated to dryness. The residue was dissolved in ethanol (30 ml.), a solution of potassium hydroxide (1.4 g.) in water (5 ml.) was added and the mixture was stirred at laboratory temperature for 2 hours and then evaporated to dryness. The residue was washed with ethyl acetate, dilute aqueous hydrochloric acid was added and the mixture was extracted with ethyl acetate. The extract was washed with water and then saturated aqueous sodium chloride solution, dried over magnesium sulphate and evaporated to dryness. There was thus obtained as residue 2-hydroxy-2-(thien-2-yl)propionic acid, which was used without further purification.

EXAMPLE 2

The process described in Example 1 was repeated except that the appropriate aniline and 2-hydroxy-2-(thien-3-yl)propionic acid (prepared by a similar process to that described in the second part of Example 1, except that 3-bromothiophene was used in place of thiophene) were used as starting materials. There were thus obtained the compounds described in the following table:

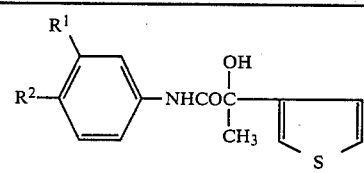

| R¹ | R² | m.p. (°C.) |
|---|---|---|
| CF₃ | NO₂ | 93–94 |
| Cl | CN | 166–167 |

EXAMPLE 3

A 1.6 molar solution of n-butyl-lithium in hexane (0.77 ml.) was added dropwise to a stirred solution of 3-bromothiophene (0.2 g.) in diethyl ether (10 ml.) which was maintained at −70° C. under an atmosphere of argon and the mixture was stirred at that temperature for 90 minutes. A solution of N-pyruvyl-3,4-dichloroaniline (0.14 g.) in tetrahydrofuran (2 ml.) was added dropwise and the mixture was stirred for 1 hour at −70° C. and then allowed to warm up to −20° C. Methanol (1 ml.) and saturated aqueous ammonium chloride solution (5 ml.) were added and the organic layer was separated, washed with water and then with saturated aqueous sodium chloride solution, dried over magnesium sulphate and evaporated to dryness. The residue was purified by chromatography on a silica gel column using a 10:1 v/v mixture of toluene and ethyl acetate as eluant. The product was crystallised from toluene and there was thus obtained N-[2-hydroxy-2-(thien-3-yl)propionyl]-3,4-dichloroaniline, m.p. 120°–121° C.

The N-pyruvyl-3,4-dichloroaniline used as starting material was obtained as follows:

Thionyl chloride (7 ml.) was added dropwise to a stirred mixture of pyruvic acid (6.7 ml.) and dimethylformamide (1.5 g.), the mixture was stirred at laboratory temperature for 2 hours and a solution of 3,4-dichloroaniline (7.7 g.) in methylene chloride (100 ml.) was added dropwise. The mixture was cooled to 0° C., a solution of triethylamine (21 ml.) in methylene chloride (40 ml.) was added dropwise and the mixture was poured into water. The organic layer was separated, the aqueous layer washed with diethyl ether, and the combined organic solutions were washed with saturated aqueous sodium bicarbonate solution and then with saturated aqueous sodium chloride solution, dried over magnesium sulphate and evaporated to dryness. The residue was crystallised from toluene and there was thus obtained N-pyruvyl-3,4-dichloroaniline, m.p. 168°–169° C.

EXAMPLE 4

3,4-Dichloroaniline (1 g.) was added to a stirred suspension of sodium hydride (0.29 g. of a 50% dispersion in mineral oil) in N,N-dimethylacetamide (30 ml.) and the mixture was stirred at laboratory temperature for 1 hour. A solution of methyl 2-hydroxy-2-(pyrid-2-yl)propionate (1.1 g.) in N,N-dimethylacetamide (10 ml.) was slowly added and the mixture was stirred at laboratory temperature for 17 hours and then poured into water. The mixture was extracted with diethyl ether and the extract was washed with water and then with saturated aqueous sodium chloride solution, dried over magnesium sulphate and evaporated to dryness. The residue was purified by chromatography on a silica gel column using toluene as eluant, and the product was crystallised from a mixture of toluene and petroleum ether (b.p. 60°–80° C.). There was thus obtained N-[2-hydroxy-2-(pyrid-2-yl)propionyl]-3,4-dichloraniline, m.p. 77.5°–78.5° C.

The methyl 2-hydroxy-2-(pyrid-2-yl)-propionate used as starting material was obtained as follows:

Trimethylsilyl cyanide (5.2 ml.) and zinc iodide (0.1 g.) were added to a stirred solution of 2-acetylpyridine (5 g.) in methylene chloride (50 ml.) and the mixture was stirred at laboratory temperature for 17 hours and then evaporated to dryness. The residue was dissolved in methanol (50 ml.), hydrogen chloride gas was bubbled through the solution for 2 hours and the mixture was poured into water. The mixture was neutralised with dilute aqueous sodium hydroxide solution and extracted with diethyl ether. The extract was washed with saturated aqueous sodium chloride solution, dried over magnesium sulphate and evaporated to dryness. The residue was purified by chromatography on a silica gel column using a 3:1 v/v mixture of toluene and ethyl acetate as eluant, and there was thus obtained methyl 2-hydroxy-2-(pyrid-2-yl)propionate which was used without further purification.

EXAMPLE 5

A 1.6 molar solution of n-butyllithium in hexane (2.9 ml.) was added dropwise to a stirred solution of 4-bromo-2-methylthiothiophene (0.83 g.) in diethyl ether (10 ml.) which was maintained at −70° C. under an atmosphere of argon, and the mixture was stirred at that temperature for 1 hour. A solution of N-pyruvyl-3,4-dichloroaniline (0.5 g.) in tetrahydrofuran (2 ml.) was added dropwise and the mixture was stirred for 1 hour at −70° C. and then allowed to warm up to −20° C. Methanol (1 ml.) and saturated aqueous ammonium chloride solution (5 ml.) were added and the organic layer was separated, washed with water and then with saturated aqueous sodium chloride solution, dried over magnesium sulphate and evaporated to dryness. The residue was purified by chromatography on a silica gel column using a 10:1 v/v mixture of toluene and ethyl acetate as eluant. There was thus obtained N-[2-hydroxy-2-(5-methylthiothien-3-yl)propionyl]-3,4-dichloroaniline as a non-crystalline gum, the structure of which was confirmed by elemental analysis and proton magnetic resonance spectroscopy.

The N-pyruvyl-3,4-dichloroaniline used as starting material was obtained as follows:

Thionyl chloride (6.6 ml.) was added to a stirred solution of pyruvic acid (8.1 g.) and N-methylpyrrolidone (17.9 ml.) in methylene chloride (75 ml.) which was maintained at −20° C., and the mixture was stirred at this temperature for 30 minutes. A solution of 3,4-dichloroaniline (11.2 g.) in methylene chloride (100 ml.) was added dropwise and the mixture was stirred at −20° C. for 30 minutes, allowed to warm up to laboratory temperature and then poured into water. The organic layer was separated, the aqueous layer washed with ethyl acetate, and the combined organic solutions were washed with saturated aqueous sodium bicarbonate solution and then with saturated aqueous sodium chloride solution, dried over magnesium sulphate and evaporated to dryness. The residue was crystallised from toluene and there was thus obtained N-pyruvyl-3,4-dichloroaniline, m.p. 168°–169° C.

EXAMPLE 6

The process described in Example 5 was repeated except that the appropriate halogenated (or non-halogenated*) heterocyclic compound was used as starting material in place of 4-bromo-2-methylthiophen, and that the appropriate aniline was used as starting material. There were thus obtained the compounds described in the following table:

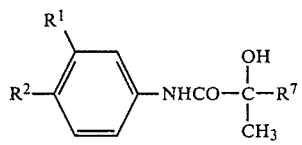

| $R^1$ | $R^2$ | $R^7$ | m.p. (°C.) |
|---|---|---|---|
| Cl | CN | 2-thienyl | 169–170* |
| $CF_3$ | $NO_2$ | 4-bromo-2-thienyl | 160–161 |
| $CF_3$ | $NO_2$ | 5-methylthio-2-thienyl | (gum)* |
| Cl | Cl | 5-methylthio-2-thienyl | (gum)* |
| Cl | CN | 5-methylthio-2-thienyl | (gum)* |
| $CF_3$ | CN | 5-methylthio-2-thienyl | (gum)* |
| Cl | $NO_2$ | 5-methylthio-2-thienyl | (gum)* |
| $CF_3$ | $NO_2$ | 5-methylthio-3-thienyl | (gum) |
| Cl | CN | 5-methylthio-3-thienyl | (gum) |

-continued

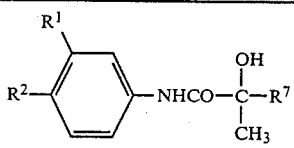

| R¹ | R² | R⁷ | m.p. (°C.) |
|---|---|---|---|
| CF₃ | NO₂ | 4-cyano-2-thienyl | 148–150+ |
| CF₃ | NO₂ | 5-cyano-2-thienyl | 158–159+ |
| Cl | CN | 5-cyano-2-thienyl | 135–137+ |
| CF₃ | CN | 5-cyano-2-thienyl | 188–189+ |
| Cl | NO₂ | 5-cyano-2-thienyl | 154–155+ |
| CF₃ | NO₂ | 5-methylthio-2-furyl | (gum)* |
| CF₃ | NO₂ | 2-thiazolyl | 106–107* |
| Cl | Cl | 2-thiazolyl | 100–101* |
| Cl | NO₂ | 2-thiazolyl | 147–148* |
| CF₃ | NO₂ | 2-chloro-5-thiazolyl | 81–84* |
| Cl | CN | 2-chloro-5-thiazolyl | 180–182* |
| CF₃ | CN | 2-chloro-5-thiazolyl | 114–115* |
| Cl | NO₂ | 2-chloro-5-thiazolyl | 145–146* |
| CF₃ | NO₂ | 2-methoxy-5-thiazolyl | 44–46* |
| CF₃ | NO₂ | 2-methoxy-4-thiazolyl | 110–112* |
| CF₃ | NO₂ | 2-methylthio-5-thiazolyl | 145–148* |
| CF₃ | NO₂ | 5-methylthio-2-thiazolyl | (gum)* |
| CF₃ | CN | 4-trifluoromethyl-2-thiazolyl | 62–65 |
| CF₃ | NO₂ | 4-trifluoromethyl-2-thiazolyl | 142–144 |
| Cl | CN | 4-trifluoromethyl-2-thiazolyl | 140–143 |
| CF₃ | NO₂ | 2-benzothiazolyl | 146–147* |
| CF₃ | NO₂ | 3-pyridyl | 178–179 |
| Cl | CN | 3-pyridyl | 204–205 |
| Cl | NO₂ | 3-pyridyl | 196–198 |
| CF₃ | NO₂ | 6-fluoro-3-pyridyl | 186–187 |
| Cl | CN | 6-fluoro-3-pyridyl | 150–151 |
| CF₃ | CN | 6-fluoro-3-pyridyl | 153–154 |
| CF₃ | NO₂ | 6-chloro-3-pyridyl | 173–175 |
| Cl | CN | 6-chloro-3-pyridyl | 190–191 |
| CF₃ | CN | 6-chloro-3-pyridyl | 188–189 |
| CF₃ | NO₂ | 6-cyano-3-pyridyl | (gum)+ |
| Cl | Cl | 6-cyano-3-pyridyl | 202–203+ |
| CF₃ | CN | 6-cyano-3-pyridyl | 232–235+ |
| CF₃ | NO₂ | 6-methoxy-3-pyridyl | (gum) |
| Cl | CN | 6-methoxy-3-pyridyl | 154–155 |
| CF₃ | CN | 6-methoxy-3-pyridyl | (gum) |
| CF₃ | NO₂ | 6-methylthio-3-pyridyl | (gum) |
| CF₃ | NO₂ | 4-pyridyl | 268–269 |
| Cl | Cl | 4-pyridyl | 226–227 |
| CF₃ | NO₂ | 5-pyrimidinyl | 267–268+ |
| Cl | Cl | 5-pyrimidinyl | 221–222+ |
| Cl | CN | 5-pyrimidinyl | 200–201+ |
| CF₃ | CN | 5-pyrimidinyl | 262–264+ |
| CF₃ | NO₂ | 1,3-dithian-2-yl | 127–129* |

*The lithiation step was carried out using a non-halogenated heterocyclic compound, as exemplified by the following preparation of the 5-methylthio-2-thienyl derivative:

A 1.6 molar solution of n-butyllithium in hexane (9.6 ml.) was added dropwise to a stirred solution of 2-methylthiophene (2.0 g.) in diethyl ether (180 ml.) which was maintained at 0° C. under an atmosphere of argon, and the mixture was stirred at this temperature for 30 minutes and then cooled to −70° C. The 5-methylthio-2-thienyllithium thus obtained was reacted with a pyruvyl-aniline exactly as described in Example 5.

+The lithiation step was carried out at −100° C. instead of −70° C.

The pyruvylaniline derivatives used as starting materials were prepared by a similar process to that described in the last part of Example 5, except that the appropriate aniline was used in place of 3,4-dichloroaniline.

EXAMPLE 7

A solution of 49% potassium hydrogen persulphate ('Oxone'; 'Oxone' is a registered Trade Mark; 5.4 g.) in water (30 ml.) was added to a stirred solution of 4-nitro-3-trifluoromethyl-N-[2-hydroxy-2-(5-methylthiothien-3-yl)propionyl]aniline (Example 6; 2.4 g.) in methanol (30 ml.) and the mixture was stirred at laboratory temperature for 17 hours, diluted with water (50 ml.) and extracted three times with chloroform (40 ml. each time). The combined extracts were washed with water and then with saturated aqueous sodium chloride solution, dried over magnesium sulphate and evaporated to dryness under reduced pressure. The residue was purified by chromatography on a silica gel column (100 g.) using a 3:2 v/v mixture of toluene and ethyl acetate as eluant, and the product was crystallised from a mixture of ethyl acetate and petroleum ether (b.p. 60°–80° C.). There was thus obtained 4-nitro-3-trifluoromethyl-N-[2-hydroxy-2-(5-methylsulphonylthien-2-yl)propionyl]aniline, m.p. 149°–151° C.

The process described above was repeated using the appropriate methylthio-substituted compound as starting material, and there were thus obtained the compounds described in the following table:

| R¹ | R² | Het | Position of —SO₂CH₃ | m.p. (°C.) |
|---|---|---|---|---|
| CF₃ | NO₂ | 2-thienyl | 5 | 184–185 |
| Cl | Cl | 2-thienyl | 5 | 193–194 |
| Cl | CN | 2-thienyl | 5 | 179–180 |
| CF₃ | CN | 2-thienyl | 5 | 194–195 |
| Cl | NO₂ | 2-thienyl | 5 | 196–198 |
| Cl | Cl | 3-thienyl | 5 | 150–151 |
| Cl | CN | 3-thienyl | 5 | 151–152 |
| CF₃ | NO₂ | 2-furyl | 5 | 174–176 |
| CF₃ | NO₂ | 5-thiazolyl | 2 | 143–145 |
| CF₃ | NO₂ | 3-pyridyl | 6 | (gum) |

EXAMPLE 8 m-Chloroperbenzoic acid (0.28 g.) was added to a stirred solution of 3,4-dichloro-N-[2-hydroxy-2-pyrid-4-yl)propionyl]aniline (0.28 g.) in methylene chloride (25 ml.) and the mixture was stirred at laboratory temperature for 17 hours, washed with saturated aqueous sodium bicarbonate solution and then with saturated sodium chloride solution, dried and evaporated to dryness. The residue was crystallised from a mixture of ethyl acetate and ethanol and there was thus obtained 3,4-dichloro-N-[2-hydroxy-2-(1-oxidopyrid-4-yl)propionyl]aniline, m.p. 219°–220° C.

The process described above was repeated using the corresponding 3-chloro-4-cyanoaniline derivative, and there was thus obtained 3-chloro-4-cyano-N-[2-hydroxy-2-(1-oxidopyrid-4-yl)propionyl]aniline, m.p. 260°–262° C.

The process described above was repeated using the corresponding 3-pyridyl derivative, and there was thus obtained 3-chloro-4-cyano-N-[2-hydroxy-2-(1-oxidopyrid-3-yl)propionyl]aniline, m.p. 263°–264° C.

What we claim is:

1. An acylanilide of the formula:

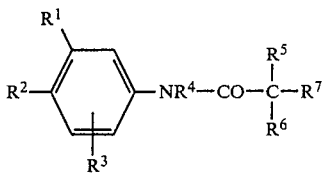

wherein $R^1$ is cyano, carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl;

wherein $R^2$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl;

wherein $R^3$ is hydrogen or halogen;

wherein $R^4$ is hydrogen or alkyl of up to 4 carbon atoms;

wherein $R^5$ is hydrogen, hydroxy, or alkoxy or acyloxy each of up to 15 carbon atoms;

wherein $R^6$ is alkyl or halogenalkyl of up to 4 carbon atoms;

and wherein $R^7$ is thienyl which is unsubstituted or bears one or two substituents selected from the group consisting of halogen, cyano, alkoxy, alkylthio, alkylsulphonyl each of up to 4 carbon atoms or trifluoromethyl.

2. An acylanilide as claimed in claim 1 wherein $R^1$ and $R^2$, which may be the same or different, each is cyano, nitro, trifluoromethyl or chloro, $R^3$ and $R^4$ are both hydrogen, $R^5$ is hydroxy, $R^6$ is methyl, and $R^7$ is 2-thienyl, 3-thienyl, which may be unsubstituted or may bear one halogen, cyano, alkoxy, alkylthio, alkylsulphonyl or trifluoromethyl substituent.

3. The compound 4-nitro-3-trifluoromethyl- or 4-cyano-3-trifluoromethyl-N-[2-hydroxy-2-(5-methanesulphonylthien-2-yl)propionyl]aniline.

4. An acylanilide according to claim 1, said acylanilide being 3-chloro-4-cyano-N-[2-hydroxy-2-(5-methanesulphonylthien-2-yl)-propionyl]aniline.

5. An acylanilide according to claim 1, said acylanilide being 4-nitro-3-trifluoromethyl-N-[2-hydroxy-2-(5-methanesulphonylthien-2-yl)propionyl]aniline.

6. An acylanilide according to claim 1, said acylanilide being 4-cyano-3-trifluoromethyl-N-[2-hydroxy-2-(5-methanesulphonylthien-2-yl)propionyl]aniline.

7. A pharmaceutical or veterinary composition which comprises an effective amount of an acylanilide, claimed in claim 1, in association with a pharmaceutically-acceptable diluent or carrier.

8. A composition as claimed in claim 7 which is in a form suitable for oral dosage, as a tablet, capsule, aqueous or oily solution or suspension or emulsion; in the form of a sterile solution or suspension suitable for parenteral administration, or in the form of an ointment or lotion for topical administration, or in the form of a suppository.

9. A method for producing an antiandrogenic effect in a warm-blooded animal in need of such treatment which comprises administering to said animal an effective amount of acylanilide claimed in claim 1.

* * * * *